United States Patent
Lansalot-Matras et al.

(10) Patent No.: US 9,691,770 B2
(45) Date of Patent: Jun. 27, 2017

(54) VANADIUM-CONTAINING FILM FORMING COMPOSITIONS AND VAPOR DEPOSITION OF VANADIUM-CONTAINING FILMS

(71) Applicant: L'Air Liquide, Société Anonyme pour l'Etude et l'Exploitation des Procédés Georges Claude, Paris (FR)

(72) Inventors: Clément Lansalot-Matras, Princeton, NJ (US); Wontae Noh, Seoul (KR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/130,558

(22) Filed: Apr. 15, 2016

(65) Prior Publication Data

US 2016/0304542 A1    Oct. 20, 2016

Related U.S. Application Data (60) Provisional application No. 62/148,261, filed on Apr. 16, 2015.

(51) Int. Cl.
| | |
|---|---|
| *H01L 27/108* | (2006.01) |
| *H01L 21/285* | (2006.01) |
| *H01L 49/02* | (2006.01) |
| *C07F 9/00* | (2006.01) |
| *C23C 16/455* | (2006.01) |

(52) U.S. Cl.
CPC ......... *H01L 27/1085* (2013.01); *C07F 9/005* (2013.01); *C23C 16/45525* (2013.01); *C23C 16/45553* (2013.01); *H01L 21/28556* (2013.01); *H01L 21/28568* (2013.01); *H01L 28/60* (2013.01)

(58) Field of Classification Search
None
See application file for complete search history.

(56) References Cited

U.S. PATENT DOCUMENTS

2008/0003359 A1* 1/2008 Gordon .................. C07C 257/14
427/248.1
2008/0038466 A1    2/2008 Reuter et al.

FOREIGN PATENT DOCUMENTS

DE    10 2006 037955    2/2008

OTHER PUBLICATIONS

Quirck, Polyhedron, vol. 1, No. 2, p. 209-11, 1982.*
Alén, P. et al., "The growth and diffusion barrier properties of atomic layer deposited $NbN_x$ thin films," Thin Solid Films 491 (2005) 235-241.
Elers, K.-E. et al., "$NbCl_5$ as a precursor in atomic layer epitaxy," Applied Surface Science 82/83 (1994) 468-474.
Elorriaga, D. et al., "Asymmetric niobium guanidinates as intermediates in the catalytic guanylation of amines," Dalton Transactions, 2013, vol. 42, Issue 23, 8223-8230.

(Continued)

*Primary Examiner* — Joseph Miller, Jr.
(74) *Attorney, Agent, or Firm* — Patricia E. McQueeney (57) ABSTRACT

Vanadium-containing film forming compositions are disclosed, along with methods of synthesizing the same, and methods of forming Vanadium-containing films on one or more substrates via vapor deposition processes using the Vanadium-containing film forming composition.

19 Claims, 1 Drawing Sheet

(56) References Cited

OTHER PUBLICATIONS

Gilmore, C.M. et al., "Stabilized zirconia-alumina thin films," J. Vac. Sci. Technol. A 4(6) Nov./Dec. 1986, 2598-2600.

Gust, K.R. et al., "Synthesis, structure, and properties of niobium and tantalum imido complexes bearing pyrazolato ligands. Crystal structures of Ta(N$t$-Bu)($t$-Bu$_2$Pz)$_3$, Ta(N$i$-Pr)($t$-Bu$_2$Pz)$_3$, Ta(N$t$-Bu)(Me$_2$Pz)$_3$(py), and Ta(N$t$-Bu)($t$-Bu$_2$Pz)$_2$(Cl)(py)," Polyhedron 20 (2001) 805-813.

Kittl, J.A. et al., "High-k dielectrics for future generation memory devices," Microelectronic Engineering 86 (2009) 1789-1795.

Maestre, M.C. et al., "Cyclopentadienyl-silyl-amido niobium complexes prepared by a transmetalation reaction using Ti{$\eta^5$-C$_5$G$_4$SiMe$_2$-$\eta$-N(CH$_2$)$_2$NRR$^3$}Cl$_2$," Organometallics 2005, 24, 5853-5857.

Ritala, M. et al., "Effects of intermediate zinc pulses on properties of TiN and NbN films deposited by atomic layer epitaxy," Applied Surface Science 120 (1997) 199-212.

Tomson, N.C. et al., "Synthesis and reactivity of cationic niobium and tantalum methyl complexes supported by imido and β-diketiminato ligands," Dalton Transactions, 2001, vol. 40, Issue 30, 7718-7729.

* cited by examiner

VANADIUM-CONTAINING FILM FORMING COMPOSITIONS AND VAPOR DEPOSITION OF VANADIUM-CONTAINING FILMS

CROSS REFERENCE TO RELATED APPLICATIONS

The present application claims the benefit of U.S. Provisional Application Ser. No. 62/148,261 filed Apr. 16, 2015, being herein incorporated by reference in its entirety for all purposes.

TECHNICAL FIELD

Vanadium-containing film forming compositions are disclosed, along with methods of synthesizing the same, and methods of forming Vanadium-containing films on one or more substrates via vapor deposition processes using the Vanadium-containing film forming compositions.

BACKGROUND

Metal Oxide films, such as Niobium Oxide ($Nb_2O_5$), have been extensively utilized in various fields of technology. Traditionally these oxides have been applied as resistive films used as high-k materials for insulating layers. For instance, a thin layer of $Nb_2O_5$ between two $ZrO_2$ dielectric layers is expected to help significantly reduce leakage current and stabilize the cubic/tetragonal phase of the $ZrO_2$, affording higher k values in the current MIM capacitor of a DRAM. (Alumina, J. Vac. Sci. Technol A 4 (6), 1986 and Microelectronic Engineering 86 (2009) 1789-1795). A thin layer of $V_2O_5$ may behave similarly.

Metal Nitride films, such as Vanadium Nitride ($VN_x$ wherein x is approximately 1) have been utilized in various fields of technology. Traditionally these nitrides have been applied as hard and decorative coatings but during the past decade they have increasingly been used as diffusion barrier and adhesion/glue layers in microelectronic devices [Applied Surface Science 120 (1997) 199-212]. $V(NMe_2)_4$ for instance has been examined as a vanadium source for chemical vapor deposition of $VN_x$ [Chemical Vapor Deposition of Vanadium, Niobium, and Tantalum Nitride Thin Films by Fix et al., Chem. Mater. 1993, 5, 614-619]. $VN_x$ films were also deposited by plasma enhanced atomic layer deposition using $V(NEtMe)_4$ and $NH_3$. [Low Temperature Plasma-Enhanced Atomic Layer Deposition of Thin Vanadium Nitride Layers for Copper Diffusion Barriers by Rampelberg et al., Appl. Phys. Lett., 102, 111910 (2013)].

Gust et al. disclose the synthesis, structure, and properties of niobium and tantalum imido complexes bearing pyrazolato ligands and their potential use for the growth of tantalum nitride films by CVD. Polyhedron 20 (2001) 805-813.

Elorriaga et al. disclose asymmetric niobium guanidinates as intermediates in the catalytic guanylation of amines (Dalton Transactions, 2013, Vol. 42, Issue 23 pp. 8223-8230).

Tomson et al. disclose the synthesis and reactivity of the cationic Nb and Ta monomethyl complexes [(BDI)MeM(NtBu)][X] (BDI=2,6-$iPr_2C_6H_3$—N—C(Me)CH—C(Me)-N(2,6-$iPr_2C_6H_3$); X=$MeB(C_6F_5)_3$ or $B(C_6F_5)_4$) (Dalton Transactions 2011 Vol. 40, Issue 30, pp. 7718-7729).

A need remains for developing liquid or low melting point (<50° C. at standard pressure), highly thermally stable, Vanadium-containing precursor molecules suitable for vapor phase film deposition with controlled thickness and composition at high temperature.

NOTATION AND NOMENCLATURE

Certain abbreviations, symbols, and terms are used throughout the following description and claims, and include:

As used herein, the indefinite article "a" or "an" means one or more.

As used herein, the terms "approximately" or "about" mean±10% of the value stated.

The standard abbreviations of the elements from the periodic table of elements are used herein. It should be understood that elements may be referred to by these abbreviations (e.g., V refers to Vanadium, N refers to nitrogen, C refers to carbon, etc.).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x (NR^2R^3)_{(4-x)}$, where x is 2 or 3, the two or three $R^1$ groups may, but need not be identical to each other or to $R^2$ or to $R^3$.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPr" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the abbreviation "amyl" refers to an amyl or pentyl group; the abbreviation "tAmyl" refers to a tert-amyl group, also known as 1,1-dimethylpropyl.

As used herein, the abbreviation "TMS" refers to trimethylsilyl ($Me_3Si$—); the abbreviation "DMS" refers to dimethylsilyl ($Me_2HSi$—); the abbreviation "MMS" refers to monomethylsilyl ($MeH_2Si$—); the abbreviation "Py" refers to pyridine; and the abbreviation $R^1,R^2,R^3$-Pyr refers to a pyrazolyl ligand having the following structure:

As used herein, the abbreviation "$N^{R, R'}R''$-amd" or $N^R$R''-amd when R=R' refers to the amidinate ligand [R—N—C(R'')=N—R'], wherein R, R' and R'' are defined alkyl groups, such as Me, Et, nPr, iPr, nBu, iBi, sBu or tBu; the abbreviation "$N^{R, R'}$-fmd" or $N^R$-fmd when R=R' refers to the formidinate ligand [R—N—C(H)=N—R'], wherein R and R' are defined alkyl groups, such as Me, Et, nPr, iPr, nBu, iBi, sBu or tBu; the abbreviation "N$^{R, R'}$, N$^{R'', R'''}$-gnd" or N$^R$, N$^{R''}$-gnd when R=R' and R''=R''' refers to the guanidinate ligand [R—N—C(NR''R''')=NR'], wherein R, R', R'' and R''' are defined alkyl group such as Me, Et, nPr, iPr, nBu, iBi, sBu or tBu. Although depicted here as having a double bond between the C and N of the ligand backbone, one of ordinary skill in the art will recognize that the amidinate, formidinate and guanidinate ligands do not contain a fixed double bond. Instead, one electron is delocalized amongst the N—C—N chain.

i) Amidinate ligand ii) Formamidinate ligand iii) Guanidinate ligand

Please note that the films or layers deposited, such as vanadium oxide, may be listed throughout the specification and claims without reference to their proper stoichoimetry (i.e., VO$_2$ or V$_2$O$_5$). The layers may include pure (V) layers, silicide (V$_o$Si$_p$) layers, carbide (V$_o$C$_p$) layers, nitride (V$_k$N$_l$) layers, oxide (V$_n$O$_m$) layers, or mixtures thereof; wherein k, l, m, n, o, and p inclusively range from 1 to 6. For instance, vanadium silicide is V$_k$Si$_l$, where k and l each range from 0.5 to 5. Similarly, any referenced layers may also include a Silicon oxide layer, Si$_n$O$_m$, wherein n ranges from 0.5 to 1.5 and m ranges from 1.5 to 3.5. More preferably, the silicon oxide layer is SiO$_2$ or SiO$_3$. The silicon oxide layer may be a silicon oxide based dielectric material, such as organic based or silicon oxide based low-k dielectric materials such as the Black Diamond II or III material by Applied Materials, Inc. Alternatively, any referenced silicon-containing layer may be pure silicon. Any referenced layers, such as the vanadium- or silicon-containing layers, may also include dopants, such as B, C, P, As and/or Ge.

Any and all ranges recited herein are inclusive of their endpoints (i.e., x=1 to 4 includes x=1, x=4, and x=any number in between), irrespective of whether the term "inclusively" is used.

SUMMARY

Disclosed are Vanadium-containing film forming compositions comprising a precursor having the formula:

wherein each R, R$^1$, R$^2$ and R$^3$ is independently H, an alkyl group, or R'$_3$Si, with each R' independently being H or an alkyl group. The disclosed Vanadium containing film forming compositions may include one or more of the following aspects:

each R independently being selected from H, Me, Et, nPr, iPr, tBu, sBu, iBu, nBu, tAmyl, SiMe$_3$, SiMe$_2$H, or SiH$_2$Me;
R, R$^1$, R$^2$ and R$^3$ being respectively tBu, H, H and H;
R, R$^1$, R$^2$ and R$^3$ being respectively tBu, Me, H and H;
R, R$^1$, R$^2$ and R$^3$ being respectively tBu, Me, H and Me;
R, R$^1$, R$^2$ and R$^3$ being respectively tBu, Et, H and Et;
R, R$^1$, R$^2$ and R$^3$ being respectively tBu, nPr, H and nPr;
R, R$^1$, R$^2$ and R$^3$ being respectively tBu, iPr, H and iPr;
R, R$^1$, R$^2$ and R$^3$ being respectively tBu, tBu, H and tBu;
R, R$^1$, R$^2$ and R$^3$ being respectively tBu, tAmyl, H and tAmyl;
R, R$^1$, R$^2$ and R$^3$ being respectively tBu, Et, H and tBu;
R, R$^1$, R$^2$ and R$^3$ being respectively tBu, iPr, H and tBu;
R, R$^1$, R$^2$ and R$^3$ being respectively tBu, iPr, H and Me;
R, R$^1$, R$^2$ and R$^3$ being respectively tBu, iPr, H and Et;
R, R$^1$, R$^2$ and R$^3$ being respectively tBu, SiMe$_3$, H and SiMe3;
R, R$^1$, R$^2$ and R$^3$ being respectively tBu, SiHMe$_2$, H and SiHMe$_2$;
R, R$^1$, R$^2$ and R$^3$ being respectively tBu, SiH$_2$Me, H and SiH$_2$Me;
R, R$^1$, R$^2$ and R$^3$ being respectively tBu, H, Me and H;
R, R$^1$, R$^2$ and R$^3$ being respectively tBu, Me, Me and H;
R, R$^1$, R$^2$ and R$^3$ being respectively tBu, Me, Me and Me;
R, R$^1$, R$^2$ and R$^3$ being respectively tBu, Et, Me and Et;
R, R$^1$, R$^2$ and R$^3$ being respectively tBu, nPr, Me and nPr;
R, R$^1$, R$^2$ and R$^3$ being respectively tBu, iPr, Me and iPr;
R, R$^1$, R$^2$ and R$^3$ being respectively tBu, tBu, Me and tBu;
R, R$^1$, R$^2$ and R$^3$ being respectively tBu, tAmyl, Me and tAmyl;
R, R$^1$, R$^2$ and R$^3$ being respectively tBu, Et, Me and tBu;
R, R$^1$, R$^2$ and R$^3$ being respectively tBu, iPr, Me and tBu;
R, R$^1$, R$^2$ and R$^3$ being respectively tBu, iPr, Me and Me;
R, R$^1$, R$^2$ and R$^3$ being respectively tBu, iPr, Me and Et;
R, R$^1$, R$^2$ and R$^3$ being respectively tBu, SiMe$_3$, Me and SiMe3;
R, R$^1$, R$^2$ and R$^3$ being respectively tBu, SiHMe$_2$, Me and SiHMe$_2$;
R, R$^1$, R$^2$ and R$^3$ being respectively tBu, SiH$_2$Me, Me and SiH$_2$Me;
R, R$^1$, R$^2$ and R$^3$ being respectively tAmyl, H, H and H;
R, R$^1$, R$^2$ and R$^3$ being respectively tAmyl, Me, H and H;
R, R$^1$, R$^2$ and R$^3$ being respectively tAmyl, Me, H and Me;
R, R$^1$, R$^2$ and R$^3$ being respectively tAmyl, Et, H and Et;
R, R$^1$, R$^2$ and R$^3$ being respectively tAmyl, nPr, H and nPr;
R, R$^1$, R$^2$ and R$^3$ being respectively tAmyl, iPr, H and iPr;

R, R¹, R² and R³ being respectively tAmyl, tBu, H and tBu;
R, R¹, R² and R³ being respectively tAmyl, tAmyl, H and tAmyl;
R, R¹, R² and R³ being respectively tAmyl, Et, H and tBu;
R, R¹, R² and R³ being respectively tAmyl, iPr, H and tBu;
R, R¹, R² and R³ being respectively tAmyl, iPr, H and Me;
R, R¹, R² and R³ being respectively tAmyl, iPr, H and Et;
R, R¹, R² and R³ being respectively tAmyl, SiMe₃, H and SiMe3;
R, R¹, R² and R³ being respectively tAmyl, SiHMe₂, H and SiHMe₂;
R, R¹, R² and R³ being respectively tAmyl, SiH₂Me, H and SiH₂Me;
R, R¹, R² and R³ being respectively tAmyl, H, Me and H;
R, R¹, R² and R³ being respectively tAmyl, Me, Me and H;
R, R¹, R² and R³ being respectively tAmyl, Me, Me and Me;
R, R¹, R² and R³ being respectively tAmyl, Et, Me and Et;
R, R¹, R² and R³ being respectively tAmyl, nPr, Me and nPr;
R, R¹, R² and R³ being respectively tAmyl, iPr, Me and iPr;
R, R¹, R² and R³ being respectively tAmyl, tBu, Me and tBu;
R, R¹, R² and R³ being respectively tAmyl, tAmyl, Me and tAmyl;
R, R¹, R² and R³ being respectively tAmyl, Et, Me and tBu;
R, R¹, R² and R³ being respectively tAmyl, iPr, Me and tBu;
R, R¹, R² and R³ being respectively tAmyl, iPr, Me and Me;
R, R¹, R² and R³ being respectively tAmyl, iPr, Me and Et;
R, R¹, R² and R³ being respectively tAmyl, SiMe₃, Me and SiMe3;
R, R¹, R² and R³ being respectively tAmyl, SiHMe₂, Me and SiHMe₂;
R, R¹, R² and R³ being respectively tAmyl, SiH₂Me, Me and SiH₂Me;
R, R¹, R² and R³ being respectively iPr, H, H and H;
R, R¹, R² and R³ being respectively iPr, Me, H and H;
R, R¹, R² and R³ being respectively iPr, Me, H and Me;
R, R¹, R² and R³ being respectively iPr, Et, H and Et;
R, R¹, R² and R³ being respectively iPr, nPr, H and nPr;
R, R¹, R² and R³ being respectively iPr, iPr, H and iPr;
R, R¹, R² and R³ being respectively iPr, tBu, H and tBu;
R, R¹, R² and R³ being respectively iPr, tAmyl, H and tAmyl;
R, R¹, R² and R³ being respectively iPr, Et, H and tBu;
R, R¹, R² and R³ being respectively iPr, iPr, H and tBu;
R, R¹, R² and R³ being respectively iPr, iPr, H and Me;
R, R¹, R² and R³ being respectively iPr, iPr, H and Et;
R, R¹, R² and R³ being respectively iPr, SiMe₃, H and SiMe3;
R, R¹, R² and R³ being respectively iPr, SiHMe₂, H and SiHMe₂;
R, R¹, R² and R³ being respectively iPr, SiH₂Me, H and SiH₂Me;
R, R¹, R² and R³ being respectively iPr, H, Me and H;
R, R¹, R² and R³ being respectively iPr, Me, Me and H;
R, R¹, R² and R³ being respectively iPr, Me, Me and Me;
R, R¹, R² and R³ being respectively iPr, Et, Me and Et;
R, R¹, R² and R³ being respectively iPr, nPr, Me and nPr;
R, R¹, R² and R³ being respectively iPr, iPr, Me and iPr;
R, R¹, R² and R³ being respectively iPr, tBu, Me and tBu;
R, R¹, R² and R³ being respectively iPr, tAmyl, Me and tAmyl;
R, R¹, R² and R³ being respectively iPr, Et, Me and tBu;
R, R¹, R² and R³ being respectively iPr, iPr, Me and tBu;
R, R¹, R² and R³ being respectively iPr, iPr, Me and Me;
R, R¹, R² and R³ being respectively iPr, iPr, Me and Et;
R, R¹, R² and R³ being respectively iPr, SiMe₃, Me and SiMe3;
R, R¹, R² and R³ being respectively iPr, SiHMe₂, Me and SiHMe₂;
R, R¹, R² and R³ being respectively iPr, SiH₂Me, Me and SiH₂Me;
R, R¹, R² and R³ being respectively tBu, iPr, Et and iPr;
R, R¹, R² and R³ being respectively tBu, iPr, nPr and iPr;
R, R¹, R² and R³ being respectively tBu, iPr, iPr and iPr;
R, R¹, R² and R³ being respectively tBu, iPr, nBu and iPr;
R, R¹, R² and R³ being respectively tBu, iPr, iBu and iPr;
R, R¹, R² and R³ being respectively tBu, iPr, sBu and iPr;
R, R¹, R² and R³ being respectively tBu, iPr, tBu and iPr;
R, R¹, R² and R³ being respectively tBu, iPr, tAmyl and iPr;
R, R¹, R² and R³ being respectively tBu, iPr, SiMe₃ and iPr;
R, R¹, R² and R³ being respectively tBu, iPr, SiHMe₂ and iPr;
R, R¹, R² and R³ being respectively tBu, iPr, SiH₂Me and iPr;

Also disclosed are V-containing film forming composition delivery devices comprising a canister having an inlet conduit and an outlet conduit and containing any of the V-containing film forming compositions disclosed above. The disclosed device may include one or more of the following aspects:
  the V-containing film forming composition having a total concentration of metal contaminants of less than 10 ppmw;
  an end of the inlet conduit end located above a surface of the V-containing film forming composition and an end of the outlet conduit located below the surface of the V-containing film forming composition;
  an end of the inlet conduit end located below a surface of the V-containing film forming composition and an end of the outlet conduit located above the surface of the V-containing film forming composition;
  further comprising a diaphragm valve on the inlet and the outlet;
  the V-containing film forming composition being V(=NtBu)(N$^{iPr}$Me-amd)₃; or
  the V-containing film forming composition being V(=NtAmyl)(N$^{iPr}$Me-amd)₃.

Also disclosed are processes for the deposition of Vanadium-containing films on substrates. The Vanadium-containing film forming composition disclosed above is introduced into a reactor having a substrate disposed therein. At least part of the precursor is deposited onto the substrate to form the Vanadium-containing film. The disclosed processes may further include one or more of the following aspects:
  introducing at least one reactant into the reactor;
  the reactant being plasma-treated;
  the reactant being remote plasma-treated;
  the reactant not being plasma-treated;
  the reactant being selected from the group consisting of H₂, H₂CO, N₂H₄, NH₃, SiH₄, Si₂H₆, Si₃H₈, SiH₂Me₂, SiH₂Et₂, N(SiH₃)₃, hydrogen radicals thereof, and mixtures thereof;

the reactant being H$_2$;
the reactant being NH$_3$;
the reactant being selected from the group consisting of: O$_2$, O$_3$, H$_2$O, H$_2$O$_2$, NO, N$_2$O, NO$_2$, oxygen radicals thereof, and mixtures thereof;
the reactant being H$_2$O;
the reactant being plasma treated O$_2$;
the reactant being O$_3$;
the Vanadium containing film forming composition and the reactant being introduced into the reactor simultaneously;
the reactor being configured for chemical vapor deposition;
the reactor being configured for plasma enhanced chemical vapor deposition;
the Vanadium containing film forming composition and the reactant being introduced into the chamber sequentially;
the reactor being configured for atomic layer deposition;
the reactor being configured for plasma enhanced atomic layer deposition;
the reactor being configured for spatial atomic layer deposition;
the Vanadium containing film being a pure V thin film;
the Vanadium containing film being V$_k$Si$_l$, wherein each of k and l is an integer which inclusively range from 1 to 6;
the Vanadium containing film being V$_n$O$_m$, wherein each of n and m is an integer which inclusively range from 1 to 6;
the Vanadium containing film being VO$_2$ or V$_2$O$_5$;
the Vanadium containing film being V$_o$N$_p$, wherein each of o and p is an integer which inclusively range from 1 to 6;
the Vanadium containing film being VN;
the Vanadium containing film being V$_o$N$_p$O$_q$, wherein each of o, p and q is an integer which inclusively range from 1 to 6; and
the Vanadium containing film being VON.

BRIEF DESCRIPTION OF THE FIGURES

For a further understanding of the nature and objects of the present invention, reference should be made to the following detailed description, taken in conjunction with the accompanying figures wherein.

DESCRIPTION OF PREFERRED EMBODIMENTS

Disclosed are Vanadium-containing film forming compositions comprising a precursor having the formula:

wherein each R, R$^1$, R$^2$ and R$^3$ are independently H, an alkyl group, or R'$_3$Si, with each R' independently being H or an alkyl group. Each R, R$^1$, R$^2$, or R$^3$ may independently be selected from H, Me, Et, nPr, iPr, tBu, sBu, iBu, nBu, tAmyl, SiMe$_3$, SiMe$_2$H, or SiH$_2$Me.

When R is iPr and each R$^2$ is H, the precursor has the formula:

When R is tBu and each R$^2$ is H, the precursor has the formula:

When R is tAmyl and each R$^2$ is H, the precursor has the formula:

In these embodiments, R$^1$ may be the same as R$^3$. For example, R$^1$ and R$^3$ may each be H, Me, Et, iPr, nPr, tBu, tAmyl, SiMe$_3$, SiHMe$_2$, or SiH$_2$Me. Alternatively, R$^1$ may differ from R$^3$. For example, R$^1$ may be Me and R$^3$ may be H. Or R$^1$ may be Et and R$^3$ may be tBu. Or R$^1$ may be iPr and R$^3$ may be Me, Et, or tBu.

When R is iPr and each R$^2$ is Me, the precursor has the formula:

When R is tBu and each R² is Me, the precursor has the formula:

When R is tAmyl and each R² is Me, the precursor has the formula:

In these embodiments, R¹ may be the same as R³. For example, R¹ and R³ may each be H, Me, Et, iPr, nPr, tBu, tAmyl, SiMe₃, SiHMe₂, or SiH₂Me. Alternatively, R¹ may differ from R³. For example, R¹ may be Me and R³ may be H. Or R¹ may be Et and R³ may be tBu. Or R¹ may be iPr and R3 may be Me, Et, or tBu.

When R is tBu, each R¹ is iPr, and each R³ is iPr, the precursor has the formula:

In these embodiments, each R² may be Et, nPr, iPr, nBu, iBu, sBu, tBu, tAmyl, SiMe₃, SiHMe₂, or SiH₂Me.

These precursors may be synthesized by reacting 1 molar equivalent of V(=NtBu)Cl₃(py)₂ with 3 molar equivalents of the relevant Lithium amidinate ligand in a polar solvent at room temperature. The Lithium amidinate ligand should be freshly prepared by reacting methyllithium with the relevant N, N-dialkylcarbodiimide as described in J Chem. Mater. 2014, 26, 3065-3073. V(=NtBu)Cl₃(py)₂ can be prepared as described in Dalton Trans., 2011, 40, 413-420. Suitable polar solvents include tetrahydrofuran (THF). After stirring for a sufficient period of time, the solvent is removed under vacuum and the product extracted using a nonpolar solvent, such as pentane.

Purity of the disclosed Vanadium-containing film forming composition is greater than 95% w/w (i.e., 95.0% w/w to 100.0% w/w), preferably greater than 98% w/w (i.e., 98.0% w/w to 100.0% w/w), and more preferably greater than 99% w/w (i.e., 99.0% w/w to 100.0% w/w). One of ordinary skill in the art will recognize that the purity may be determined by H NMR or gas or liquid chromatography with mass spectrometry. The disclosed Vanadium-containing film forming compositions may contain any of the following impurities: N,N-dialkylcarbodiimide, amidine; pyridines; alkylamines; alkylimines; THF; ether; pentane; cyclohexane; heptanes; benzene; toluene; chlorinated metal compounds; or lithium, sodium, or potassium amidinate. The total quantity of these impurities is below 5% w/w (i.e., 0.0% w/w to 5.0% w/w), preferably below 2% w/w (i.e., 0.0% w/w to 2.0% w/w), and more preferably below 1% w/w (i.e. 0.0% w/w to 1.0% w/w). The composition may be purified by recrystallisation, sublimation, distillation, and/or passing the gas or liquid through a suitable adsorbent, such as a 4A molecular sieve.

Purification of the disclosed Vanadium-containing film forming composition may also result in metal impurities at the 0 ppbw to 1 ppmw, preferably 0-500 ppbw (part per billion weight) level. These metal impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and Zinc (Zn).

The V-containing film forming composition that have a low melting point (i.e., melt at a temperature below 50° C.) and/or exhibit low residue (i.e., between 0% and 10%) during thermogravimetric analysis are expected to be suitable for vapor deposition processes.

Figure 1:
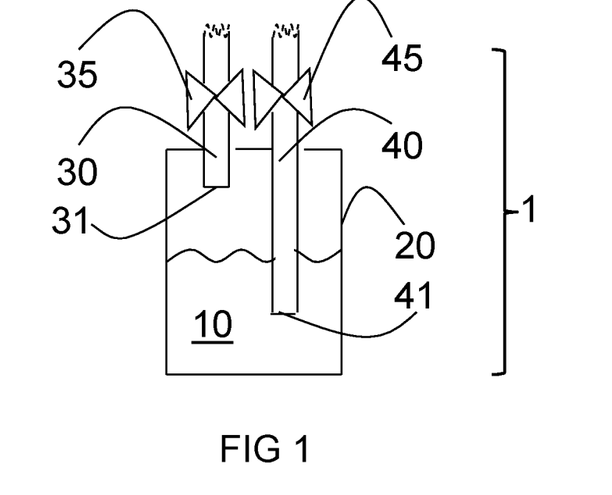
FIG. 1 is a side view of one embodiment of the V-containing film forming composition delivery device.
Figure 2:
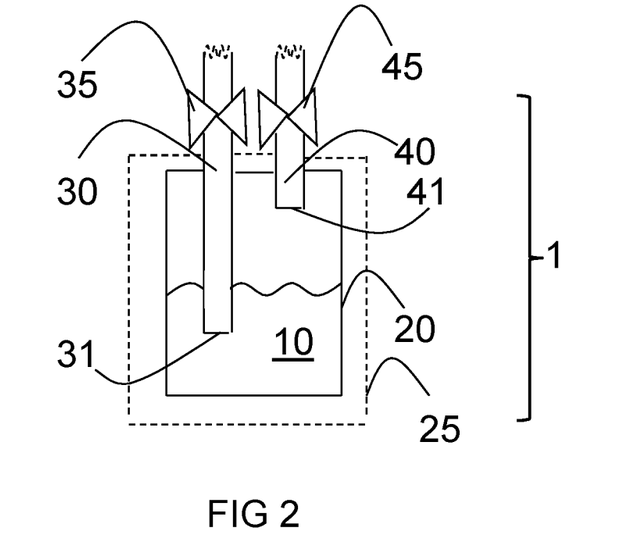
FIG. 2 is a side view of a second embodiment of the V-containing film forming composition delivery device.

The disclosed V-containing film forming compositions may be delivered to a semiconductor processing tool by the disclosed V-containing film forming composition delivery devices. FIGS. 1 and 2 show two embodiments of the disclosed delivery devices 1.

FIG. 1 is a side view of one embodiment of the V-containing film forming composition delivery device 1. In FIG. 1, the disclosed V-containing film forming composition 10 are contained within a container 20 having two conduits, an inlet conduit 30 and an outlet conduit 40. One of ordinary skill in the precursor art will recognize that the container 20, inlet conduit 30, and outlet conduit 40 are manufactured to prevent the escape of the gaseous form of the V-containing film forming composition 10, even at elevated temperature and pressure.

Suitable valves include spring-loaded or tied diaphragm valves. The valve may further comprise a restrictive flow orifice (RFO). The delivery device should be connected to a gas manifold and in an enclosure. The gas manifold should permit the safe evacuation and purging of the piping that may be exposed to air when the delivery device is replaced so that any residual amounts of the material do not react. The enclosure should be equipped with sensors and fire control capability to control the fire in the case of a pyrophoric material release. The gas manifold should also be equipped with isolation valves, vacuum generators, and permit the introduction of a purge gas at a minimum.

The delivery device must be leak tight and be equipped with valves that do not permit escape of even minute amounts of the material. The delivery device fluidly connects to other components of the semiconductor processing tool, such as the gas cabinet disclosed above, via valves 35 and 45. Preferably, the delivery device 20, inlet conduit 30, valve 35, outlet conduit 40, and valve 45 are made of 316L EP or 304 stainless steel. However, one of ordinary skill in the art will recognize that other inert materials, such as Hastelloy or Inconel, may also be used in the teachings herein to prevent any potential contamination of the V-containing film forming composition 10.

In FIG. 1, the end 31 of inlet conduit 30 is located above the surface of the V-containing film forming composition 10, whereas the end 41 of the outlet conduit 40 is located below the surface of the V-containing film forming composition 10. In this embodiment, the V-containing film forming composition 10 is preferably in liquid form. An inert gas, including but not limited to nitrogen, argon, helium, and mixtures thereof, may be introduced into the inlet conduit 30. The inert gas pressurizes the delivery device 20 so that the liquid V-containing film forming composition 10 is forced through the outlet conduit 40 and to components in the semiconductor processing tool (not shown). The semiconductor processing tool may include a vaporizer which transforms the liquid V-containing film forming composition 10 into a vapor, with or without the use of a carrier gas such as helium, argon, nitrogen or mixtures thereof, in order to deliver the vapor to a chamber where a wafer to be repaired is located and treatment occurs in the vapor phase. Alternatively, the liquid V-containing film forming composition 10 may be delivered directly to the wafer surface as a jet or aerosol.

FIG. 2 is a side view of a second embodiment of the V-containing film forming composition delivery device 1. In FIG. 2, the end 31 of inlet conduit 30 is located below the surface of the V-containing film forming composition 10, whereas the end 41 of the outlet conduit 40 is located above the surface of the V-containing film forming composition 10. FIG. 2 also includes an optional heating element 25, which may increase the temperature of the V-containing film forming composition 10. The V-containing film forming composition 10 may be in solid or liquid form. An inert gas, including but not limited to nitrogen, argon, helium, and mixtures thereof, is introduced into the inlet conduit 30. The inert gas flows through the V-containing film forming composition 10 and carries a mixture of the inert gas and vaporized V-containing film forming composition 10 to the outlet conduit 40 and to the components in the semiconductor processing tool.

Both FIGS. 1 and 2 include valves 35 and 45. One of ordinary skill in the art will recognize that valves 35 and 45 may be placed in an open or closed position to allow flow through conduits 30 and 40, respectively. Either delivery device 1 in FIG. 1 or 2, or a simpler delivery device having a single conduit terminating above the surface of any solid or liquid present, may be used if the V-containing film forming composition 10 is in vapor form or if sufficient vapor pressure is present above the solid/liquid phase. In this case, the V-containing film forming composition 10 is delivered in vapor form through the conduit 30 or 40 simply by opening the valve 35 in FIG. 1 or 45 in FIG. 2, respectively. The delivery device 1 may be maintained at a suitable temperature to provide sufficient vapor pressure for the V-containing film forming composition 10 to be delivered in vapor form, for example by the use of an optional heating element 25.

While FIGS. 1 and 2 disclose two embodiments of the V-containing film forming composition delivery device 1, one of ordinary skill in the art will recognize that the inlet conduit 30 and outlet conduit 40 may both be located above or below the surface of the V-containing film forming composition 10 without departing from the disclosure herein. Furthermore, inlet conduit 30 may be a filling port. Finally, one of ordinary skill in the art will recognize that the disclosed V-containing film forming compositions may be delivered to semiconductor processing tools using other delivery devices, such as the ampoules disclosed in WO 2006/059187 to Jurcik et al., without departing from the teachings herein.

Also disclosed are methods for forming Vanadium-containing layers on a substrate using a vapor deposition process. The method may be useful in the manufacture of semiconductor, photovoltaic, LCD-TFT, or flat panel type devices. The disclosed Vanadium-containing film forming compositions may be used to deposit Vanadium-containing films using any deposition methods known to those of skill in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, PE-ALD, or spatial ALD in order to provide suitable step coverage and film thickness control.

The disclosed Vanadium-containing film forming compositions may consist of the precursor or a combination of the precursor and a suitable solvent, such as ethyl benzene, xylene, mesitylene, decalin, decane, dodecane, and mixtures thereof. The disclosed precursors may be present in varying concentrations in the solvent.

The Vanadium-containing film forming compositions are introduced into a reactor in vapor form by conventional means, such as tubing and/or flow meters.

The vapor form may be produced by vaporizing the composition through a conventional vaporization step such as direct vaporization, distillation, or by bubbling, or by using a sublimator such as the one disclosed in PCT Publication WO2009/087609 to Xu et al. The composition may be fed in liquid state to a vaporizer where it is vaporized before it is introduced into the reactor. Alternatively, the composition may be vaporized by passing a carrier gas into a container containing the composition or by bubbling the carrier gas into the composition. The carrier gas may include, but is not limited to, Ar, He, $N_2$, and mixtures thereof. Bubbling with a carrier gas may also remove any dissolved oxygen present in the composition. The carrier gas and composition are then introduced into the reactor as a vapor.

If necessary, the container containing the disclosed composition may be heated to a temperature that permits the composition to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the compounds to react and form the layers. One of ordinary skill in the art will recognize that any of these reactors may be used for either ALD or CVD deposition processes.

The reactor contains one or more substrates onto which the films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, plastic or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper layers or noble metal layers (e.g. platinum, palladium, rhodium, or gold). The wafers may include barrier layers, such as manganese, manganese oxide, etc. Plastic layers, such as poly(3,4-ethylenedioxythiophene)poly(styrenesulfonate) [PEDOT:PSS] may also be used. The layers may be planar or patterned. The disclosed processes may deposit the Vanadium-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. For example, a Vanadium Nitride film may be deposited onto a Si layer. In subsequent processing, a zirconium oxide layer may be deposited on the Vanadium Nitride layer, a second Vanadium Nitride layer may be deposited on the zirconium oxide layer forming a VN/ZrO$_2$/VN stack which may be used in DRAM capacitors.

The temperature and the pressure within the reactor are held at conditions suitable for vapor depositions. In other words, after introduction of the vaporized composition into the chamber, conditions within the chamber are such that at least part of the precursor is deposited onto the substrate to form a Vanadium-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 400° C. One of ordinary skill in the art will recognize that "at least part of the precursor is deposited" means that some or all of the precursor reacts with or adheres to the substrate.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 400° C. Alternatively, when a thermal process is performed, the deposition temperature may range from approximately 200° C. to approximately 500° C.

In addition to the disclosed Vanadium-containing film forming composition, a reactant may be introduced into the reactor. The reactant may be $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof. Preferably, the reactant is $H_2$ or $NH_3$.

Alternatively, the reactant may be an oxidizing gas such as one of $O_2$, $O_3$, $H_2O$, $H_2O_2$, NO, $N_2O$, $NO_2$, oxygen containing radicals such as O• or OH•, carboxylic acids, formic acid, acetic acid, propionic acid, and mixtures thereof. Preferably, the oxidizing gas is selected from the group consisting of $O_2$, $O_3$, or $H_2O$.

The reactant may be treated by a plasma, in order to decompose the reactant into its radical form. $N_2$ may also be utilized as a nitrogen source gas when treated with plasma. For instance, the plasma may be generated with a power ranging from about 50 W to about 500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Vanadium-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O• radicals. Preferably, the remote plasma may be generated with a power ranging from about 1 kW to about 10 kW, more preferably from about 2.5 kW to about 7.5 kW.

The vapor deposition conditions within the chamber allow the disclosed composition and the reactant to react and form a Vanadium-containing film on the substrate. In some embodiments, Applicants believe that plasma-treating the reactant may provide the reactant with the energy needed to react with the disclosed precursors.

Depending on what type of film is desired to be deposited, an additional precursor compound may be introduced into the reactor. The additional precursor may be used to provide additional elements to the Vanadium-containing film. The additional elements may include lanthanides (Ytterbium, Erbium, Dysprosium, Gadolinium, Praseodymium, Cerium, Lanthanum, Yttrium), zirconium, germanium, silicon, magnesium, titanium, manganese, ruthenium, bismuth, lead, magnesium, aluminum, or mixtures of these. When an additional precursor compound is utilized, the resultant film deposited on the substrate contains the Vanadium metal in combination with an additional element.

The Vanadium-containing film forming composition and reactants may be introduced into the reactor either simultaneously (chemical vapor deposition), sequentially (atomic layer deposition) or different combinations thereof. The reactor may be purged with an inert gas between the introduction of the compositions and the introduction of the reactants. Alternatively, the reactants and the compositions may be mixed together to form a reactant/composition mixture, and then introduced to the reactor in mixture form. Another example is to introduce the reactant continuously and to introduce the Vanadium-containing film forming composition by pulse (pulsed chemical vapor deposition).

The vaporized composition and the reactant may be pulsed sequentially or simultaneously (e.g. pulsed CVD) into the reactor. Each pulse of composition may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each may last for a time period ranging from about 0.01 seconds to about 10 seconds, alternatively from about 0.3 seconds to about 3 seconds, alternatively from about 0.5 seconds to about 2 seconds. In another alternative, the vaporized compositions and reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD process, the vapor phase of the disclosed Vanadium-containing film forming composition and a reactant are simultaneously introduced into the reactor. The two react to form the resulting Vanadium-containing film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD process, the vapor phase of the disclosed Vanadium-containing film forming composition is introduced into the reactor, where it is contacted with a suitable substrate. Excess composition may then be removed from the reactor by purging and/or evacuating the reactor. A reactant (for example, $NH_3$) is introduced into the reactor where it reacts with the absorbed composition in a self-limiting manner. Any excess reactant is removed from the reactor by purging and/or evacuating the reactor. If the desired film is a Vanadium Nitride, this two-step process may provide the desired film thickness or may be repeated until a film having the necessary thickness has been obtained.

Alternatively, if the desired film contains the Vanadium transition metal and a second element, the two-step process above may be followed by introduction of the vapor of an additional precursor compound into the reactor. The additional precursor compound will be selected based on the nature of the Vanadium-containing film being deposited. After introduction into the reactor, the additional precursor compound is contacted with the substrate. Any excess precursor compound is removed from the reactor by purging and/or evacuating the reactor. Once again, a reactant may be introduced into the reactor to react with the precursor compound. Excess reactant is removed from the reactor by purging and/or evacuating the reactor. If a desired film thickness has been achieved, the process may be terminated. However, if a thicker film is desired, the entire four-step process may be repeated. By alternating the provision of the Vanadium-containing film forming composition, additional precursor compound, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

In a second non-limiting exemplary ALD process, the vapor phase of one of the disclosed Vanadium-containing film forming composition, for example Vanadium (tbutyl imido) tris(3,5-diisopropylpyrazolyl) (V(=NtBu)(iPr,H,iPr-Pyr)$_3$), is introduced into the reactor, where it is contacted with a Si substrate. Excess composition may then be removed from the reactor by purging and/or evacuating the reactor. A reactant (for example, $NH_3$) is introduced into the reactor where it reacts with the absorbed composition in a self-limiting manner to form a Vanadium Nitride film. Any excess $NH_3$ gas is removed from the reactor by purging and/or evacuating the reactor. These two steps may be repeated until the Vanadium Nitride film obtains a desired thickness, typically around 10 angstroms. $ZrO_2$ may then be deposited on the VN film. For example, $ZrCp(NMe_2)_3$ may serve as the Zr precursor. The second non-limiting exemplary ALD process described above using V(=NtBu)(iPr,H, iPr-Pyr)$_3$ and $NH_3$ may then be repeated on the $ZrO_2$ layer. The resulting VN/$ZrO_2$/VN stack may be used in DRAM capacitors.

In a third non-limiting exemplary ALD process, the vapor phase of one of the disclosed Vanadium-containing film forming composition, for example Vanadium tButyl imido N, N'-diisopropylamidinate (V(=NtBu)(N$^{iPr}$ Me-amd)$_3$), is introduced into the reactor, where it is contacted with a Si substrate. Excess composition may then be removed from the reactor by purging and/or evacuating the reactor. A reactant (for example, $NH_3$) is introduced into the reactor where it reacts with the absorbed composition in a self-limiting manner to form a Vanadium Nitride film. Any excess $NH_3$ gas is removed from the reactor by purging and/or evacuating the reactor. These two steps may be repeated until the Vanadium Nitride film obtains a desired thickness, typically around 10 angstroms. $ZrO_2$ may then be deposited on the VN film. For example, $ZrCp(NMe_2)_3$ may serve as the Zr precursor. The third non-limiting exemplary ALD process described above using V(=NtBu)(N$^{iPr}$ Me-amd)$_3$ and $NH_3$ may then be repeated on the $ZrO_2$ layer. The resulting VN/$ZrO_2$/VN stack may be used in DRAM capacitors.

The Vanadium-containing films resulting from the processes discussed above may include V, $V_kSi_l$, $V_nO_m$, $V_oN_p$, or $V_oN_pO_q$, wherein k, l, m, n, o, p, and q may each independently range from 1 to 6. Exemplary films include $VO_2$, $V_2O_5$, VN, and VON. One of ordinary skill in the art will recognize that by judicial selection of the appropriate Vanadium-containing film forming composition and reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the VN film may be exposed to a temperature ranging from approximately 200° C. and approximately 1000° C. for a time ranging from approximately 0.1 second to approximately 7200 seconds under an inert atmosphere, a N-containing atmosphere, or combinations thereof. Most preferably, the temperature is 400° C. for 3600 seconds under an inert atmosphere or a N-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon contamination of the VN film. This in turn tends to improve the resistivity of the film.

After annealing, the Vanadium-containing films deposited by any of the disclosed processes may have a bulk resistivity at room temperature of approximately 50 μohm.cm to approximately 1,000 μohm.cm. Room temperature is approximately 20° C. to approximately 28° C. depending on the season. Bulk resistivity is also known as volume resistivity. One of ordinary skill in the art will recognize that the bulk resistivity is measured at room temperature on VN films that are typically approximately 50 nm thick. The bulk resistivity typically increases for thinner films due to changes in the electron transport mechanism. The bulk resistivity also increases at higher temperatures.

In another alternative, the disclosed compositions may be used as doping or implantation agents. Part of the disclosed composition may be deposited on top of the film to be doped, such as an indium oxide ($In_2O_3$) film, tantalum dioxide ($TaO_2$), niobium dioxide ($NbO_2$) film, titanium oxide film, copper oxide film, or tin dioxide ($SnO_2$) film. The Vanadium then diffuses into the film during an annealing step to form the Vanadium-doped films {(V)$In_2O_3$, (V)$NbO_2$, (V)TiO, (V)CuO, (V)$SnO_2$}. See, e.g., US2008/0241575 to Lavoie et al., the doping method of which is incorporated herein by reference in its entirety.

Alternatively, high energy ion implantation using a variable energy radio frequency quadrupole implanter may be used to dope the Vanadium of the disclosed compositions into a film. See, e.g., Kensuke et al., JVSTA 16(2) March/April 1998, the implantation method of which is incorporated herein by reference in its entirety. In another alternative, plasma doping, pulsed plasma doping or plasma immersion ion implantation may be performed using the disclosed compositions. See, e.g., Felch et al., Plasma doping for the fabrication of ultra-shallow junctions Surface Coatings Technology, 156 (1-3) 2002, pp. 229-236, the doping method of which is incorporated herein by reference in its entirety.

EXAMPLE

The following non-limiting example is provided to further illustrate embodiments of the invention. However, the examples are not intended to be all inclusive and are not intended to limit the scope of the inventions described herein.

Example

Prophetic Synthesis of Vanadium tButyl imido N, N'-diisopropylamidinate

To a solution of V(=NtBu)$Cl_3$(py)$_2$ (X mol) in THF at −78° C., add dropwise a solution of freshly prepared lithium N, N'-diisopropylamidinate from the reaction of N,N'-diisopropylcarbodiimide (3× mol) and methyllithium (excess mol in ether). Stir overnight at room temperature. Remove the solvent under vacuum and extract the product with pentane. Purify the material using either distillation or sublimation It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:
1. A Vanadium-containing film forming composition comprising a precursor having the formula wherein each R, $R^1$, $R^2$ and $R^3$ is independently H, an alkyl group, or $R'_3Si$, with each R' independently being H or an alkyl group.

2. The Vanadium-containing film forming composition of claim 1, wherein R is iPr and each $R^2$ is H.

3. The Vanadium-containing film forming composition of claim 1, wherein R is iPr and each $R^2$ is Me.

4. The Vanadium-containing film forming composition of claim 1, wherein R is tBu and each $R^2$ is H.

5. The Vanadium-containing film forming composition of claim 1, wherein R is tBu and each $R^2$ is Me.

6. The Vanadium-containing film forming composition of claim 5, wherein each $R^1$ and $R^3$ is iPr.

7. The Vanadium-containing film forming composition of claim 1, wherein R is tAmyl and each $R^2$ is H.

8. The Vanadium-containing film forming composition of claim 1, wherein R is tAmyl and each $R^2$ is Me.

9. The Vanadium-containing film forming composition of claim 1, wherein R is tBu, each $R^1$ is iPr, and each $R^3$ is iPr.

10. A method of forming a Vanadium-containing film, the method comprising introducing into a reactor having a substrate therein a vapor of the Vanadium-containing film forming composition of claim 1; and depositing at least part of the precursor onto the substrate.

11. The method of claim 10, further comprising introducing a reactant into the reactor.

12. The method of claim 11, wherein the reactant is selected from the group consisting of $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof.

13. The method of claim 11, wherein the reactant is selected from the group consisting of $O_2$, $O_3$, $H_2O$, $H_2O_2$, $NO$, $N_2O$, $NO_2$, oxygen radicals thereof, and mixtures thereof.

14. The method of claim 11, wherein the Vanadium-containing film forming composition and the reactant are introduced into the reactor simultaneously and the reactor is configured for chemical vapor deposition.

15. The method of claim 11, wherein the Vanadium-containing film forming composition and the reactant are introduced into the chamber sequentially and the reactor is configured for atomic layer deposition.

16. The method of claim 10, wherein the substrate is a dielectric layer.

17. The method of claim 16, wherein the substrate is $ZrO_2$ and the Vanadium-containing film forming composition is used to form a DRAM capacitor.

18. The method of claim 11, further comprising plasma treating the reactant.

19. The method of claim 11, wherein the Vanadium-containing film forming precursor is $V(=NtBu)(N^{iPr}$ Me-amd$)_3$ or $V(=NtAmyl)(N^{iPr}$ Me-amd$)_3$ and the reactant is $NH_3$ or $O_3$.

\* \* \* \* \*